(12) United States Patent
Grahek et al.

(10) Patent No.: US 8,435,938 B2
(45) Date of Patent: May 7, 2013

(54) PURE VANCOMYCIN HYDROCHLORIDE

(75) Inventors: Rok Grahek, Kranj (SI); Andrej Bastarda, Vrhnika (SI)

(73) Assignee: Lek Pharmaceuticals d.d., Ljubljana, Slovenia ( * ) Notice: Subject to any disclaimer, the term of this patent is extended or adjusted under 35 U.S.C. 154(b) by 1049 days.

(21) Appl. No.: 11/720,893

(22) PCT Filed: Dec. 5, 2005

(86) PCT No.: PCT/EP2005/012998
§ 371 (c)(1),
(2), (4) Date: Apr. 14, 2010

(87) PCT Pub. No.: WO2006/061166
PCT Pub. Date: Jun. 15, 2006

(65) Prior Publication Data
US 2010/0190958 A1    Jul. 29, 2010

(30) Foreign Application Priority Data
Dec. 7, 2004    (SI) .................................. P200400334

(51) Int. Cl.
*A61K 38/04*    (2006.01)
*A61K 38/12*    (2006.01)
*C07K 7/54*    (2006.01)

(52) U.S. Cl.
USPC ............. 514/2.6; 514/2.7; 514/21.1; 530/317

(58) Field of Classification Search ........................ None
See application file for complete search history.

(56) References Cited

U.S. PATENT DOCUMENTS

| 5,149,784 A | 9/1992 | Chu et al. |
| 5,258,495 A | 11/1993 | Chu et al. |
| 5,854,390 A | 12/1998 | Grahek et al. |
| 6,391,851 B1 | 5/2002 | Sawai et al. |

FOREIGN PATENT DOCUMENTS

CN    1415758    5/2003

OTHER PUBLICATIONS

United States Pharmacopeia. 2003, pp. 1930-1931.*

* cited by examiner

*Primary Examiner* — Noble Jarrell
(74) *Attorney, Agent, or Firm* — Luedeka Neely Group, P.C.

(57) ABSTRACT

The new pure vancomycin hydrochloride substantially free of impurities known in commercially available products is described. The term "substantially free of impurities" designates a purity of vancomycin hydrochloride between about 97% and about 99%, particularly between about 98% and about 99%, preferably about 99%, as determined by HPLC analytical method as directed in U.S.P., NF 27th revision, 22 (2004). The new pure vancomycin hydrochloride (vancomycin B hydrochloride) contains less than 0.7% of total impurities, namely, only one impurity exceeds 0.3%. The new process for the purification of crude vancomycin by displacement chromatography is described by which the desired pure antibiotic according to the present invention is produced, based on the finding that high purity of the vancomycin hydrochloride is obtained using low selected pH values of the mobile phase between 3.9 and 4.2. Vancomycin hydrochloride is the known antibiotic which is used for the treatment of severe staphylococcal infections, especially those caused by methicillin-resistant staphylococcal strains.

9 Claims, 3 Drawing Sheets

PURE VANCOMYCIN HYDROCHLORIDE

Figure 1:
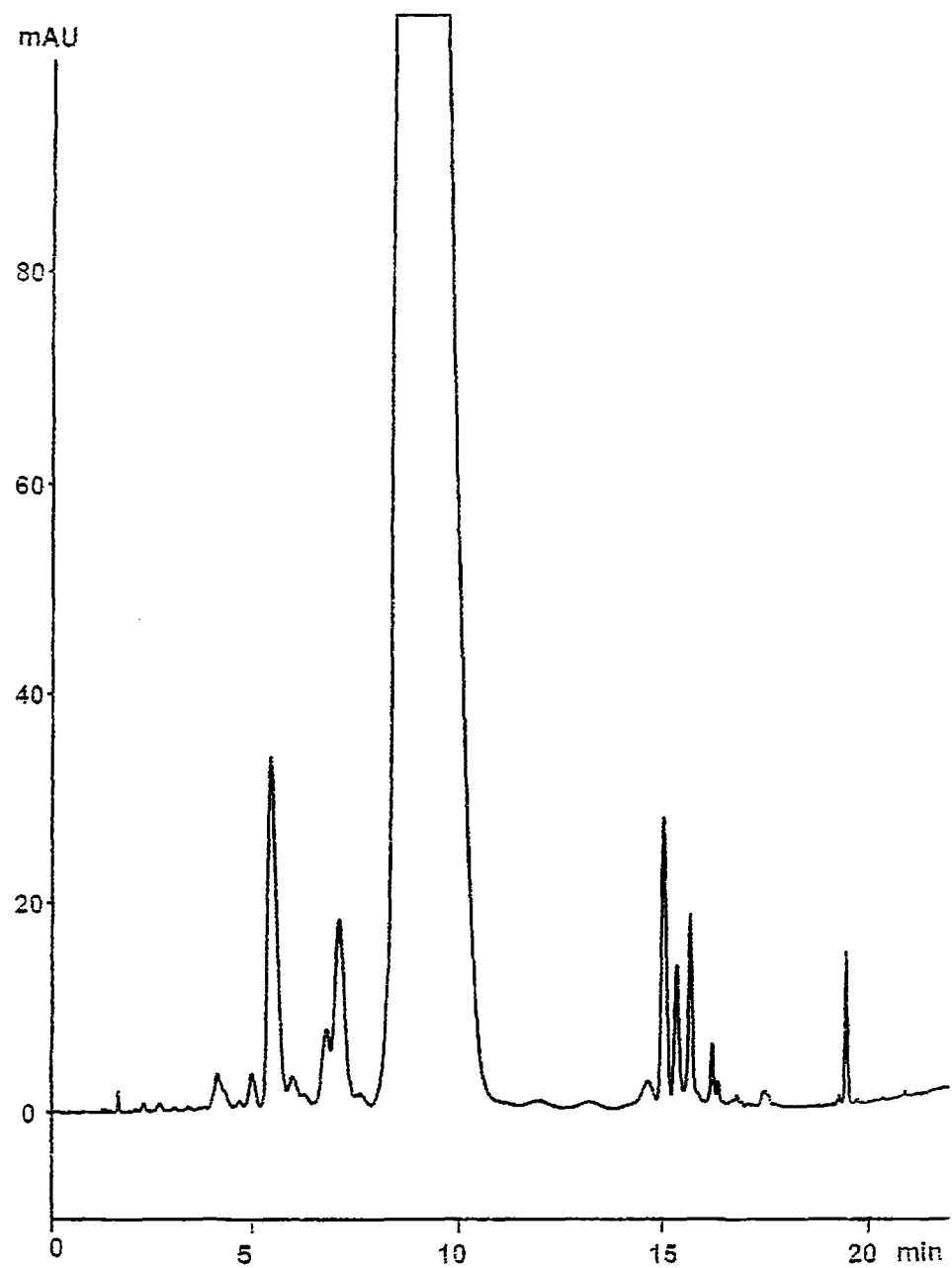

This application is the National stage of International Application No. PCT/EP2005/012998, filed on Dec. 5, 2005, which claims benefit under 35 U.S.C §119 (e) of Slovenian patent application P200400334, filed on Dec. 7, 2004, the contents of both are incorporated herein by reference in their entirety.

FIELD OF THE INVENTION (Int. Cl.: C 07 K 5/12, A 61 K 38/12)

The present invention belongs to the field of medicinally active substances from the group of glycopeptide antibiotics and relates to pure vancomycin hydrochloride substantially free of impurities known in commercially available products and having a purity ranging from about 97% to about 99%, as well as to a new process for the purification of vancomycin by use of preparative HPLC, that is, the method of displacement chromatography.

Vancomycin hydrochloride is used for the treatment of severe staphylococcal infections, especially those caused by methicillin-resistant staphylococcal strains.

TECHNICAL PROBLEM

For antibiotics and vancomycin hydrochloride, specifically, because of accompanying impurities and consequently possible side effects, a high purity of the antibiotic is desired for certain types of use in patients. Therefore, there is a constant need for pure vancomycin hydrochloride substantially free of accompanying impurities and a process by which such a product would be prepared.

PRIOR ART

Vancomycin is a tricyclic amphoteric glycopeptide antibiotic used in therapy in the form of its hydrochloride salt and is also cited in The Merck Index, An Encyclopedia of Chemicals, Drugs and Biologicals, 13 th ed. (2001), under Monograph no. 9995. It was first disclosed in U.S. Pat. No. 3,067,099. Vancomycin hydrochloride is used for the treatment of staphylococcal infections, especially infections caused by methicillin-resistant staphylococcal strains. Vancomycin is a fermentation product isolated from a fermentation broth of *Nocardia orientalis* (formerly *Streptomyces orientalis* such as, for example, *Streptomyces orientalis* NRRL 2452) which produces a mixture of related co-fermentative factors. "Factor B" (vancomycin B) is identified as the most important antibiotic in the mixture and is available in commercial products. The vancomycin fermentation broth is filtered and the filtrate is added to a column that contains an adsorption resin that decolorizes and desalts vancomycin. The resin is washed and eluted with a solvent of low pH, and the eluate is then decolorized with active carbon. The vancomycin eluate is subsequently purified using a crystallization step at low pH of the medium. The crystallized vancomycin is combined with hydrochloric acid and precipitated in an organic solvent such as acetone to form vancomycin hydrochloride.

Vancomycin hydrochloride is used orally or parenterally, and it is in the form of a dry substance as a dry off-white powder in sterile vials or small bottles. The dry solid form of vancomycin is obtained by lyophilization of the aqueous solutions of its hydrochloride salt, and with water, it forms a clear solution having a pH between 2.5 and 4.5.

Literature describes a number of processes for the preparation of vancomycin and hydrochloride salt thereof, from the fermentation medium disclosed in the above U.S. Pat. No. 3,067,099 and other literature describing precipitation processes with alkali hydroxide, such as sodium hydroxide described in U.S. Pat. No. 5,037,652 or U.S. Pat. No. 5,235,037; processes for the purification with imidazole vancomycin complex, described in U.S. Pat. No. 4,868,285; via the formation of phosphates described in patent EP 145 484, via the formation of complexes with peptides disclosed in U.S. Pat. No. 4,667,024 or by adsorption onto different polymer resins disclosed in U.S. Pat. No. 4,440,753 or U.S. Pat. No. 4,874,843.

U.S. Pat. No. 5,574,135 discloses an improved process for the manufacture of crystalline vancomycin which consists of passing a vancomycin fermentation broth through two adsorbents successively, producing a purified vancomycin. Purified vancomycin is then crystallized from the solution by adding an alkali base solution to impart a pH between 9.0 and 9.5 to the medium. It is disclosed that the vancomycin obtained is of greater purity than vancomycin produced by other prior art processes. The vancomycin purity is about 90% after two crystallization steps.

U.S. Pat. No. 5,854,390 discloses a new process for the purification of vancomycin by High Pressure Liquid Chromatography, that is, by the method of displacement chromatography, whereby chromatographic purity of 95.5% of the vancomycin hydrochloride is essentially improved. The chromatography is performed on a reverse stationary phase with a mobile phase consisting of an organic or inorganic acid or an appropriate buffer, and with different displacing agents, at a defined pH, temperature, and amount and concentration of vancomycin. According to the disclosed process, the portion of impurities that vancomycin hydrochloride contains is one-third lower than in hitherto known commercially available products.

The method of displacement chromatography is known and described in the literature, e.g., in the article of G. Subramanian et al., "Displacement Chromatography of Biomolecules," J. Chromatography, vol. 439, (1988), pp. 341-351, and is based on the principle that in a sample the balance between stationary phase and mobile phase is shifted in the direction of stationary phase. Single components of the sample displace each other, and the displacing agent of the greater affinity to stationary phase pushes the components of the mixture out of the column.

U.S. Pat. No. 4,885,275 discloses new and stable concentrated aqueous solutions of vancomycin hydrochloride without accompanying gel as well as a new process for lyophilization of vancomycin hydrochloride obtained in the form of dry, freely soluble and flowing powder from the said concentrated solutions.

DESCRIPTION OF THE INVENTION INCLUDING EXAMPLES

An object of the present invention is to solve the problem known in the prior art, that is, to manufacture a new pure vancomycin hydrochloride substantially free of impurities, known in commercially available products, according to the new process for chromatographic purification of vancomycin by which vancomycin hydrochloride of exceptionally high purity will be obtained. The term "substantially free of impurities" used herein in reference to pure vancomycin hydrochloride means a purity of about 97% to about 99%, preferably about 98% to about 99%, most preferably about 99%, determined by HPLC analytical method as directed in *The United States Pharmacopeia, The National Formulary NF*, 27$^{th}$ revision, 22 (2004), Monograph: "*Vancomycin Hydro-*

*chloride.*" The term pure vancomycin hydrochloride used herein means vancomycin B hydrochloride identified as the major factor of vancomycin hydrochloride in commercial products.

U.S. Pat. No. 5,854,390 discloses a process for the purification of vancomycin by displacement chromatography on the reverse stationary phase at a pH of the mobile phase between about 2 to about 10, preferably between about 2 to about 6, while the example presents the mobile phase pH of 3.0. After applying vancomycin dissolved in the mobile phase onto the column, it is displaced by a displacing agent out of the column, the fractions are collected, and the combined fractions are lyophilized according to their quality. The particle size of the stationary (reverse) phase is within the range from a few μm to several 100 μm, wherein the example gives the particle size of the stationary phase of 12 μm.

Unexpectedly and surprisingly, we have found that the problem known in the prior art is solved by using the new process for the purification of crude vancomycin by displacement chromatography with a stationary phase (reverse phase) of the selected narrow pH of the mobile phase between 3.9 and 4.2 using the particle size of the stationary phase within the range from a few μm to several 100 μm, preferably with the selected particle size of the stationary phase of 5 μm. The stationary phase is octadecyl silica gel.

The process for the purification of crude vancomycin (an aqueous solution with a pH of 3.2) by displacement chromatography on a reverse phase according to the present invention comprises the following steps:

a) conditioning the column having a stationary phase with the pH of the mobile phase between 3.9 and 4.2;
b) applying crude vancomycin dissolved in the mobile phase onto the column;
c) applying a displacing agent to displace vancomycin out of the column and collecting the fractions of the eluate;
d) combining and concentrating the fractions of the eluate with a purity exceeding 97%;
e) adjusting the pH of the vancomycin solution with an aqueous solution of ammonia or alkaline base to a pH between 8.5 and 9.0;
f) suspending the separated vancomycin salt from step e) in water and adjusting the medium with hydrochloric acid to a pH of about 3.0 to about 3.5;
g) precipitation of vancomycin hydrochloride from the solution with an organic solvent;
h) isolation of pure vancomycin hydrochloride.

The column is conditioned with an appropriate mobile phase. The pH of the mobile phase must be moderately acidic because of a lower stability of vancomycin in an alkaline medium and is adjusted with an appropriate acid or an appropriate buffer to the pH of 3.9 to 4.2. The mobile phase can be with water-diluted solutions of organic or inorganic acids, such as acetic acid, formic acid, propionic acid, hydrochloric acid, boric acid, phosphoric acid, sulfuric acid, or buffers formed with alkali metal cations, ammonia or amine, such as sodium acetate, ammonium acetate or ammonium phosphate. To achieve a better wetting of the stationary phase, an amount of a few percentages (about 3%) of a lower $C_1$-$C_4$ alcohol, such as methanol, ethanol, acetonitrile or a combination thereof, may be added to the mobile phase. Crude vancomycin dissolved in the mobile phase is loaded onto a column, then a displacing agent to displace vancomycin with a concentration between 5 and 150 mg/ml of the mobile phase, and the fractions of the vancomycin eluate with a purity exceeding about 97% are collected. The combined and concentrated fractions of the vancomycin eluate are concentrated to a concentration of vancomycin between 50 and 150 mg/ml according to their purity quality. An appropriate solvent, such as menthanol, is then added to the concentrate, the medium is adjusted with an aqueous solution of alkaline base or ammonium hydroxide to a pH between 8.5 to 9.0, and the resulting vancomycin solution is chilled to a temperature between −20° C. and 5° C. The separated vancomycin salt is filtered off, resuspended in water, and the medium is adjusted with hydrochloric acid to a pH between 3.0 and 3.5, and vancomycin hydrochloride is precipitated from an aqueous solution in an organic solvent, such as isopropanol. The obtained pure vancomycin hydrochloride is filtered off and dried under vacuum at a temperature of 30° C.

We have found that the best results are obtained if a pH of the combined vancomycin eluates with purity exceeding 97% is adjusted to a pH between 8.5 and 9.0 of the vancomycin solution with an aqueous solution of ammonia or alkali base. The alkali base may be sodium hydroxide, potassium hydroxide, or an alkaline-earth hydroxide, such as calcium hydroxide and others.

For the preparation of the commercial form of vials, the pure vancomycin hydrochloride is lyophilized by methods known in the prior art.

The purity of vancomycin hydrochloride is determined by High Pressure Liquid Chromatography analytical method as directed in *The United States Pharmacopeia, The National Formulary,* $27^{th}$ revision, 22 (2004), Monograph: "*Vancomycin Hydrochloride.*"

Figure 2:
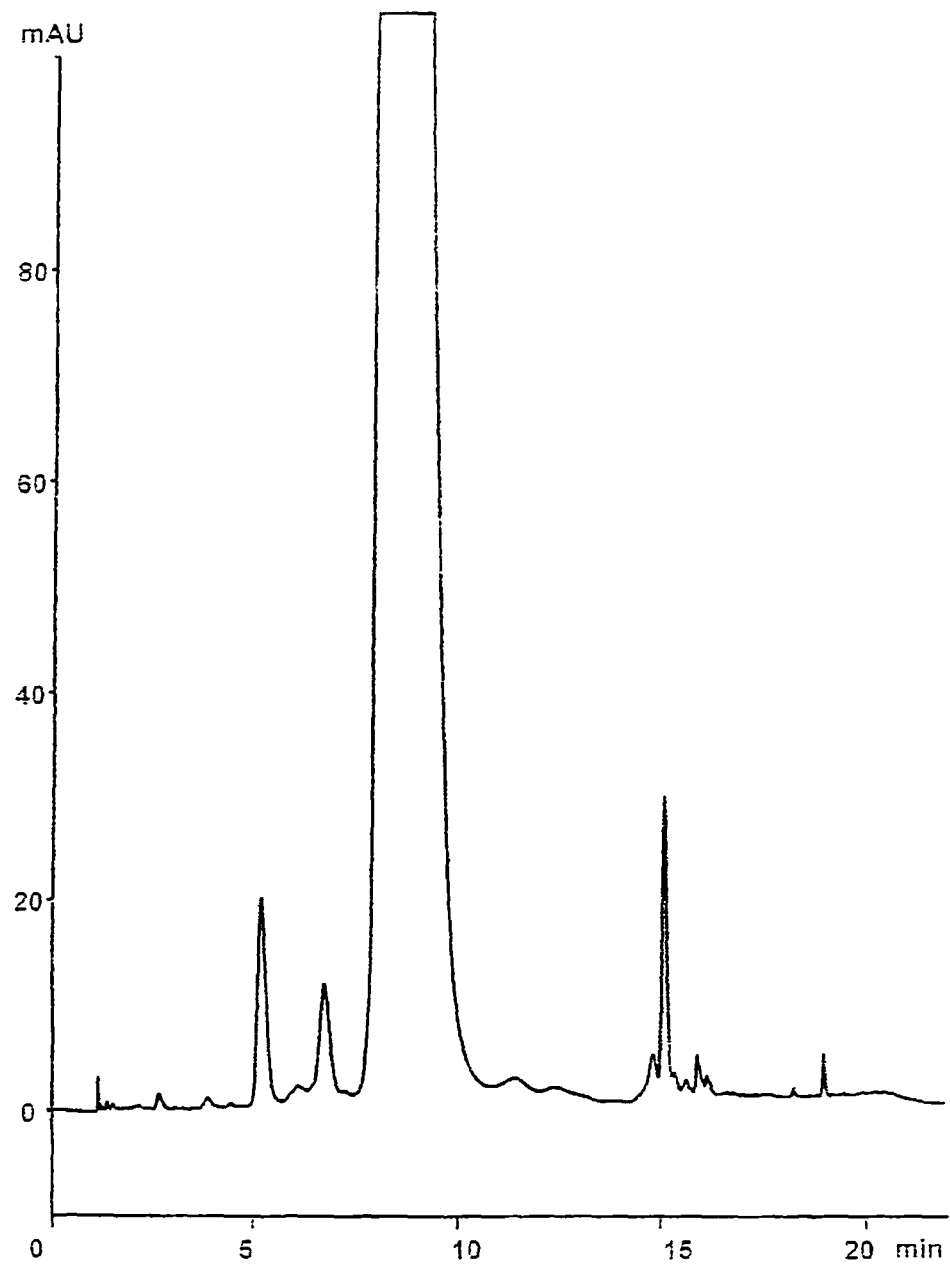
Figure 3:
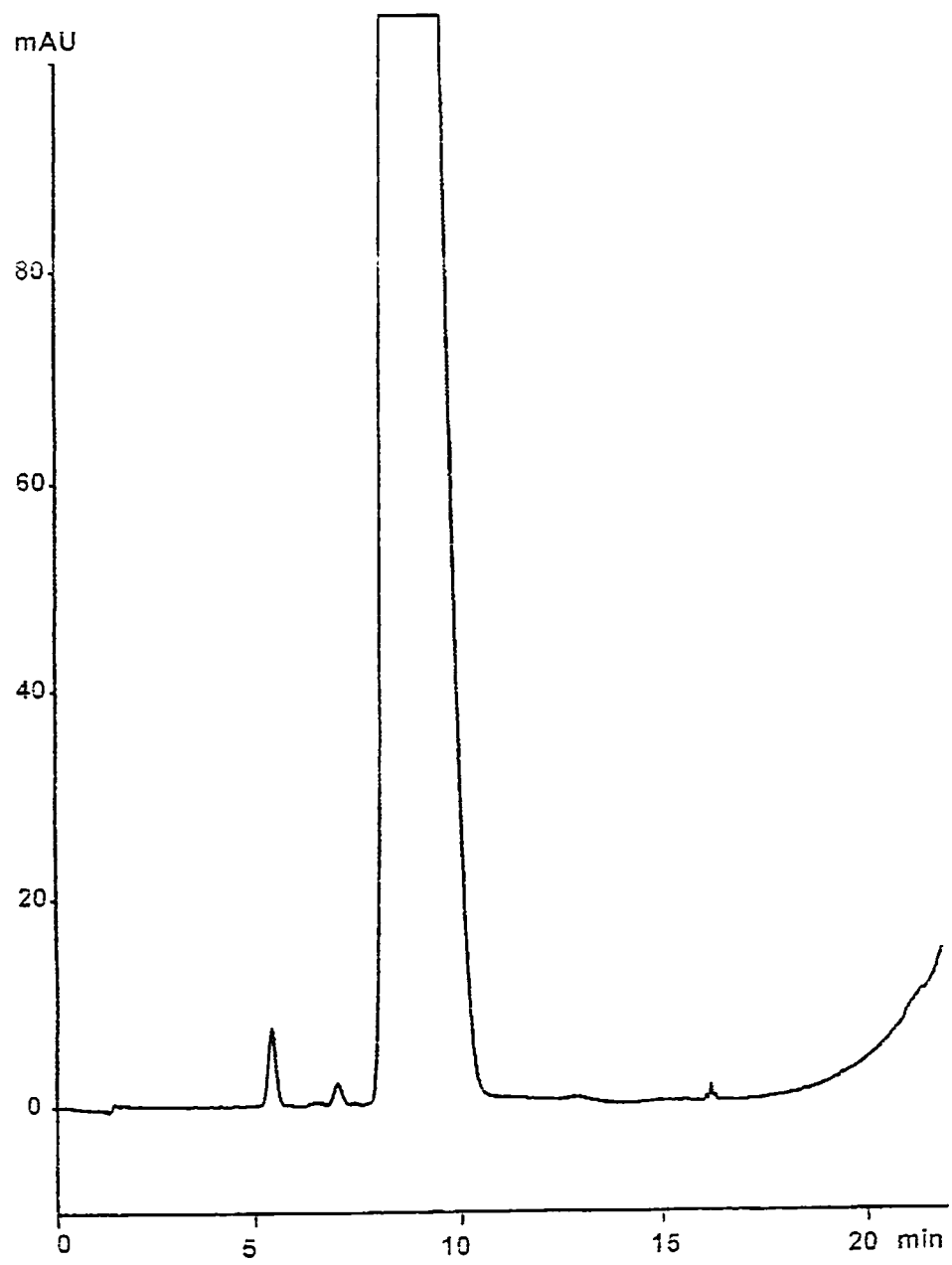

According to the process of the present invention, the pure vancomycin hydrochloride is produced substantially free of impurities known in commercially available products and in a high total yield. According to the above-mentioned HPLC analytical method, the number and the percent portion of impurities were determined in the samples of commercially available vancomycin hydrochloride (see Vancomycin Hydrochloride, USP, manufacturer American Pharmaceutical Partners, Lot: 130373, Exp.: 04/05, in which vancomycin hydrochloride was prepared according to the process disclosed in U.S. Pat. No. 5,854,390 ) and in the sample of vancomycin hydrochloride prepared according to the present invention. In the commercially available sample of vancomycin hydrochloride, twelve (12) impurities were detected in the assay in amounts greater than 0.1%, of which five (5) impurities assayed above 0.3% as illustrated in the chromatogram in FIG. 1. FIG. 2 illustrates the chromatogram of the sample of vancomycin hydrochloride prepared as disclosed in U.S. Pat. No. 5,854,390. In contrast to the prior art and the commercially available product, only two (2) impurities determined with the assay were above 0.1%, of which only one (1) impurity above 0.3% was detected in the pure vancomycin prepared according to the present invention. This means that the new vancomycin hydrochloride of the present invention contains less than 0.7% of total impurities, that is, only one impurity greater than 0.3%. FIG. 3 illustrates the chromatogram of the sample of vancomycin hydrochloride prepared according to the present invention.

The displacing agent is selected from the group consisting of:
a higher n-alcohol with $C_4$-$C_{10}$ carbon atoms;
a (di)oxyalcohol (alcohol-ether)—a compound of the type R—O—Y—OH or R—O—Y—O—Y—OH with an ether bond and a hydroxyl end, wherein R is a $C_{1-12}$ alkyl radical and Y is an alkylene group;
a quaternary ammonium salt with the general formula $R_1R_2R_3R_4NX$, wherein $R_1$, $R_2$, $R_3$ and $R_4$ being the same or different represent phenyl, benzyl or a $C_{1-12}$ alkyl radical, and X is chloride, bromide or iodide;
sodium dodecyl sulfate or a hydroxyl derivative thereof.

Preferably, n-pentanol in the form of a solution is used in the mobile phase.

The starting crude and partially purified vancomycin may be prepared by the procedures known in the prior art. Vancomycin is a fermentation product which can be isolated, for example, from a fermentation broth of *Streptomyces orientalis* NRRL 2425 by filtration of the vancomycin fermentative broth and the filtrate is added to a column that contains an adsorption resin that decolorizes and desalts the vancomycin. The resin is washed, and the vancomycin is eluted with an appropriate solvent of low pH of the medium, followed by decolorization of the eluate with active carbon. The vancomycin eluate is then further purified using crystallization at low pH of the medium. The crystallized vancomycin is combined with hydrochloric acid and precipitated in an organic solvent, such as acetone, to form vancomycin hydrochloride.

Preferably, vancomycin from a fermentation broth of *Streptomyces orientalis* is isolated and partially purified as disclosed in U.S. Pat. No. 5,853,720; thereafter, mycelia and other solid substances are separated from the fermentation broth of *Streptomyces orientalis* by microfiltration separation. The resulting permeate is partially purified on an Amberlite XAD 16 acrylate resin column and after eluting with an appropriate solvent, such as acidic methanol (addition of acidic acid), the combined eluates are concentrated by reverse osmosis. The concentrate is then purified with active carbon to produce a decolorized concentrate of the (crude) vancomycin, which is loaded on a column according to the present invention.

The present invention further relates to the use of the new pure vancomycin hydrochloride for manufacturing the medicinal product for the treatment of bacterial infections and the lyophilized pure vancomycin hydrochloride in sterile form in vials and suitable for injection use.

The present invention is illustrated, but is in no way limited, by the following example.

EXAMPLE

A process for purification of crude vancomycin by displacement chromatography

The stationary phase is a YMC-pack ODS-AQ octadecyl silica gel column (reverse phase) 20×250 mm with a particle size of 5 µm (YMC Co. Ltd., Kyoto, Japan). The mobile phase consists of a 5 mM aqueous solution of ammonium acetate with an added 3% part of methanol (V/V), and the pH of the medium is adjusted to 4.0 with acetic acid. The displacing agent is a 2% solution of n-pentanol in the mobile phase. The sample for loading on the column is 25 ml of an aqueous solution of crude vancomycin (pH adjusted to 3.2 with hydrochloric acid and having a concentration of vancomycin of 100 mg/ml) to which 9.6 mg of ammonium acetate and 0.75 ml of methanol are added, and the pH is adjusted to 4.0 with an addition of an aqueous solution of ammonia or acetic acid. The flow rate of the mobile phase, the displacing agent, and the sample load is 8 ml/min.

The column, washed with 250 ml of the mobile phase, is loaded with the sample, then washed for one minute first with the mobile phase, and subsequently the displacing agent is applied. When vancomycin emerge in the eluate, the fractions are collected every 2 minutes. When the concentration of vancomycin in the eluate decreases to half of the maximum concentration, fraction collection is stopped, and the column is washed with 250 ml of methanol. The column is then further washed with the mobile phase.

The fractions of the eluate with a chromatographic purity greater than 97.5% (as determined by HPLC analytical method according to already mentioned directions from USP 27-NF 22, 2004) are combined and concentrated under vacuum to a concentration of vancomyin of 140 mg/ml. To 12.5 ml of the resulting concentrate, 100 ml of methanol is added first, then the medium is adjusted to a pH from about 8.5 to 9.0 with a 1M aqueous solution of ammonia, and the resulting solution is chilled to 0° C. The separated precipitate is filtered off, washed with 20 ml of 0° C.-chilled methanol, and then suspended in 10 ml of water while stirring the medium with a pH adjusted to 3.2 with 2M hydrochloric acid to effect dissolution of the precipitate. To the resulting solution, 50 ml of isopropanol is added, chilled to 0° C. and filtered off, and the resulting vancomycin hydrochloride is dried under vacuum at a temperature of 30° C. 1.5 g (a 60% yield) of pure vancomycin B hydrochloride is obtained as a white powder and at a purity of 99.3% (as determined by HPLC analytical method according to USP 27-NF 22, 2004) and is stored in polyethylene "Alu-Alu bags" under nitrogen atmosphere.

The invention claimed is:

1. A process for the purification of vancomycin comprising the following steps:
   a) conditioning the column having a stationary phase with the pH of the mobile phase between 3.9 and 4.2;
   b) applying crude vancomycin dissolved in the mobile phase onto the column;
   c) applying a displacing agent to displace vancomycin out of the column and collecting the fractions of the eluate;
   d) combining and concentrating the fractions of the eluate with a purity exceeding 97%;
   e) adjusting a pH of the vancomycin solution with an aqueous solution of ammonia or alkaline base to a pH between 8.5 and 9.0;
   f) suspending the separated vancomycin salt from step e) in water and adjusting the medium with hydrochloric acid to a pH of about 3.0 to about 3.5;
   g) precipitation of vancomycin hydrochloride from the solution with an organic solvent;
   h) isolation of pure vancomycin hydrochloride.

2. The process according to claim 1a), wherein the stationary phase is octadecyl silica gel with the particle size of 5 µm.

3. The process according to claim 1a), wherein the mobile phase is an organic or inorganic acid selected from the group consisting of acetic acid, formic acid, propionic acid, hydrochloric acid, boric acid, phosphoric acid, sulfuric acid or buffers of alkali metal cations with ammonia or amines selected from the group consisting of sodium acetate, ammonium acetate, ammonium phosphate or mixtures thereof, also containing a lower $C_1$-$C_4$ alcohol or acetonitrile.

4. The process according to claim 3, wherein the lower $C_1$-$C_4$ alcohol is methanol or ethanol.

5. The process according to claim 1a), wherein the mobile phase consists of an aqueous solution of ammonium acetate, methanol and acetic acid.

6. The process according to claim 1e), wherein a pH of the vancomycin solution is adjusted with an aqueous solution of ammonia or alkali base selected from the group consisting of sodium hydroxide, potassium hydroxide or alkaline-earth hydroxide.

7. The process according to claim 1c), wherein the displacing agent is selected from the group consisting of:
   a higher n-alcohol with $C_4$-$C_{10}$ carbon atoms;
   a (di)oxyalcohol (alcohol-ether)—a compound of the type R—O—Y—OH or R—O—Y—O—Y—OH with an ether bond and a hydroxyl end, wherein R is a $C_{1-12}$ alkyl radical, and Y is an alkylene group;

a quaternary ammonium salt with the general formula $R_1R_2R_3R_4NX$, wherein $R_1$, $R_2$, $R_3$ or $R_4$ is the same or different and represent phenyl, benzyl or a $C_{1-12}$ alkyl radical, and X is chloride, bromide or iodide;
sodium dodecyl sulfate or a hydroxyl derivative thereof.

8. The process according to claim 1c), wherein the displacing agent is a solution of n-pentanol in the mobile phase.

9. The process according to claim 1g), wherein the organic solvent is isopropanol.

* * * * *